United States Patent
Shino et al.

(10) Patent No.: US 9,289,284 B2
(45) Date of Patent: Mar. 22, 2016

(54) LIGAMENT SCREW ATTACHMENT DEVICE

(71) Applicant: Smith & Nephew, Inc., Memphis, TN (US)

(72) Inventors: Konsei Shino, Osaka (JP); Michael Charles Ferragamo, Foster, RI (US); Jeffrey Wyman, Naples, FL (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

(21) Appl. No.: 14/318,769

(22) Filed: Jun. 30, 2014

(65) Prior Publication Data

US 2014/0316463 A1  Oct. 23, 2014

Related U.S. Application Data

(62) Division of application No. 13/300,406, filed on Nov. 18, 2011, now Pat. No. 8,821,498.

(51) Int. Cl.
*A61F 2/08* (2006.01)
*A61B 17/04* (2006.01)

(52) U.S. Cl.
CPC .......... *A61F 2/0811* (2013.01); *A61B 17/0401* (2013.01); *A61B 2017/0404* (2013.01); *A61B 2017/044* (2013.01); *A61B 2017/0409* (2013.01); *A61B 2017/0414* (2013.01); *A61B 2017/0453* (2013.01); *A61B 2017/0458* (2013.01); *A61F 2002/087* (2013.01); *A61F 2002/0829* (2013.01); *A61F 2002/0882* (2013.01)

(58) Field of Classification Search
CPC ......... A61F 2/08; A61F 2/0811; A61B 17/04; A61B 17/0401
USPC .......... 606/92–94, 105, 144, 148, 228, 232; 623/13.11–13.19
See application file for complete search history.

(56) References Cited

U.S. PATENT DOCUMENTS

| | | | |
|---|---|---|---|
| 4,955,910 A | 9/1990 | Bolesky | |
| 8,496,705 B2 | 7/2013 | Hart | |
| 2005/0065533 A1* | 3/2005 | Magen et al. | 606/102 |
| 2006/0200236 A1* | 9/2006 | Bianchi et al. | 623/13.14 |
| 2007/0162122 A1* | 7/2007 | Whittaker | 623/13.14 |
| 2010/0324676 A1* | 12/2010 | Albertorio et al. | 623/13.14 |
| 2013/0172998 A1 | 7/2013 | Whittaker | |

FOREIGN PATENT DOCUMENTS

| | | |
|---|---|---|
| WO | 9901084 | 1/1999 |
| WO | 0149207 | 7/2001 |
| WO | 0230262 | 4/2002 |

OTHER PUBLICATIONS

International Search Report for related International Application No. PCT/US2012/064754 mailed Feb. 26, 2013.

* cited by examiner

*Primary Examiner* — Christopher Beccia
(74) *Attorney, Agent, or Firm* — Burns & Levinson LLP; Joseph M. Maraia

(57) ABSTRACT

A bone block assembly including a bone block having a proximal end, a distal end, a central axis defined therethrough, and a hole formed therethrough, and a threaded screw having a proximal end, a distal end, and a first eyelet formed on the proximal end of the threaded screw, the threaded screw configured to be received within the hole of the bone block. The first eyelet of the threaded screw is, at least partially, exposed on the proximal end of the bone block when the threaded screw is fully engaged with the bone block. The first eyelet of the threaded screw is configured to receive a suture.

16 Claims, 12 Drawing Sheets

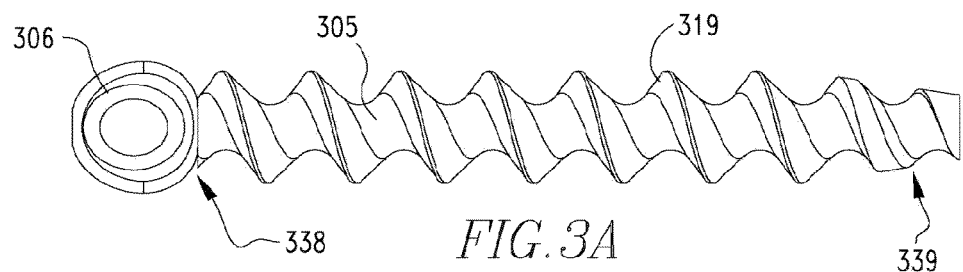
FIG.3A
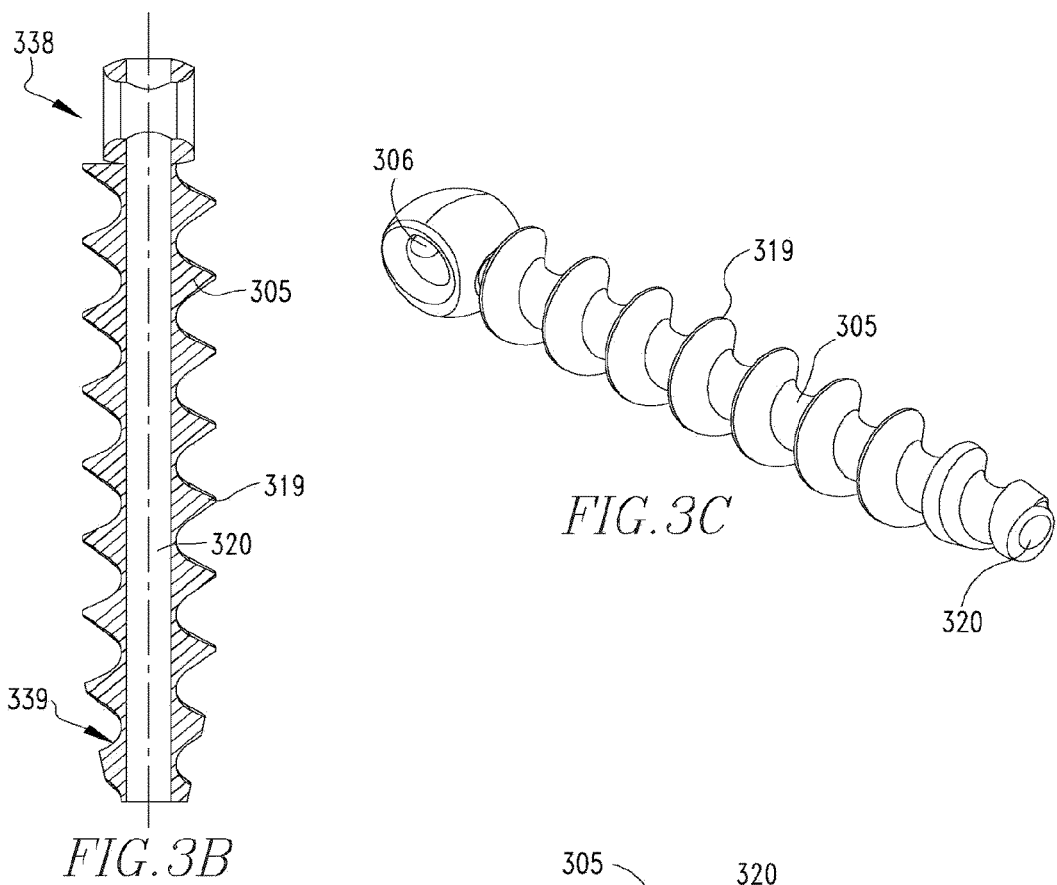
FIG.3B
FIG.3C
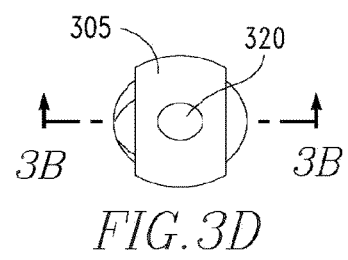
FIG.3D

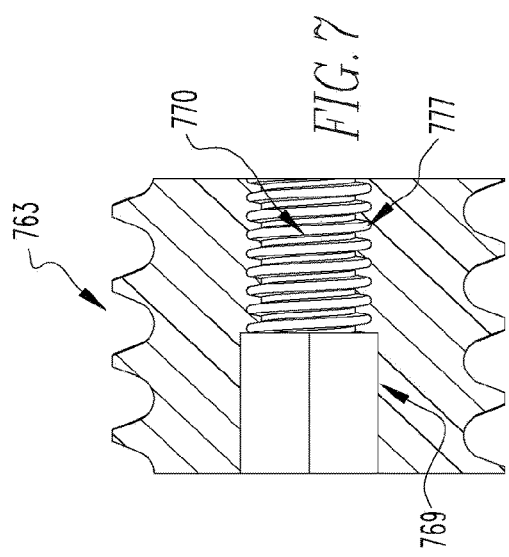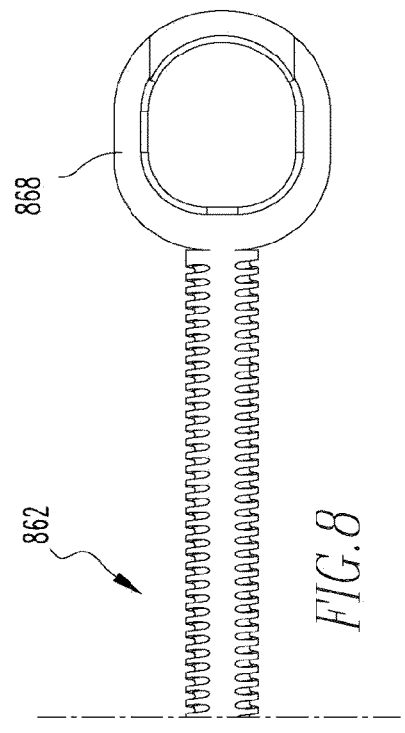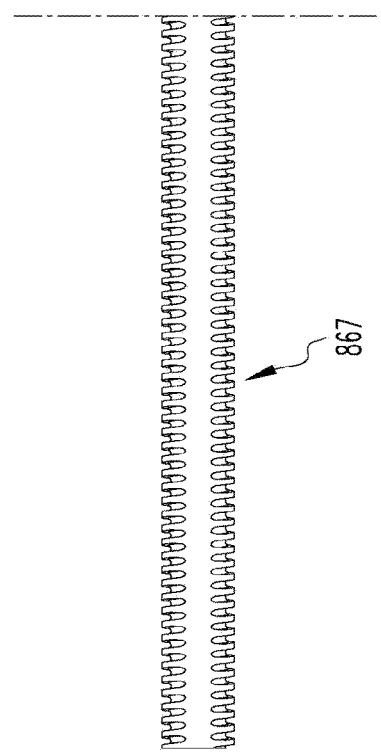

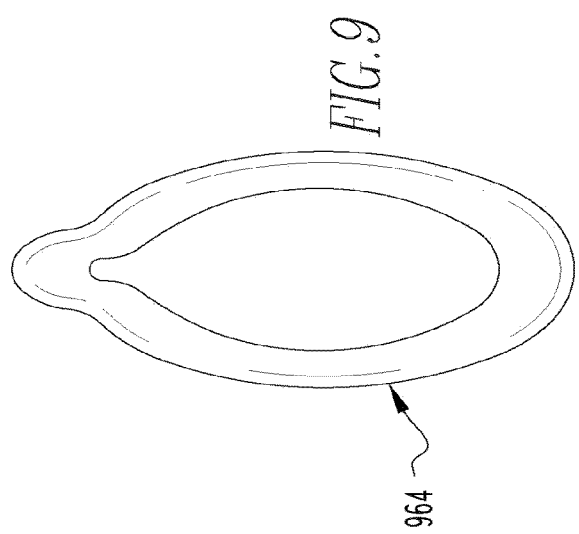
FIG. 9
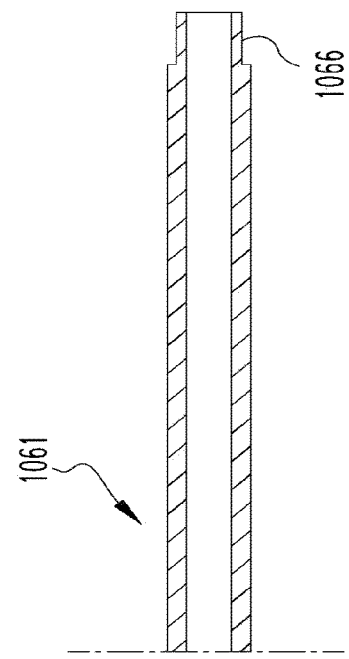
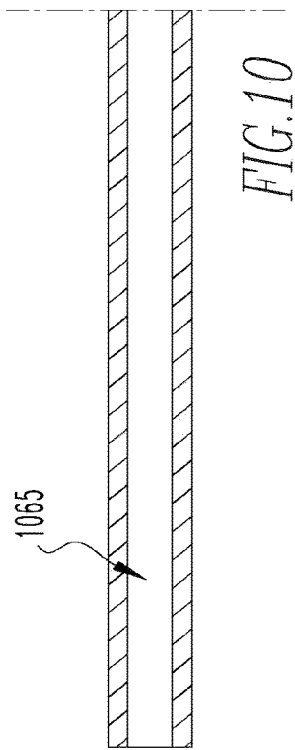
FIG. 10

_US 9,289,284 B2_

LIGAMENT SCREW ATTACHMENT DEVICE

CROSS-REFERENCE TO RELATED APPLICATIONS

This application is a divisional of U.S. application Ser. No. 13/300,406, filed Nov. 18, 2011, the contents of which is incorporated by reference.

BACKGROUND

In arthroscopic surgery, a torn or ruptured ligament or tendon may be treated by attaching an end of a tendon or ligament graft to bone. The graft end may be secured to the bone by any of a variety of devices and techniques. One common procedure, for example, involves the replacement of the anterior cruciate ligament (ACL) of the knee. In such operations, a tunnel is typically prepared through the patient's tibia, across the interarticular joint and into the femur. A hamstring tendon graft or a bone-tendon-bone graft may be attached to an implantable graft fixation device or screw or the like which is frequently planted in the femoral tunnel to help anchor one end of the graft therein. The other end of the graft is secured in the bone tunnel in the tibia or otherwise secured to the tibia.

Known configurations of such implantable devices incorporate various methods of mounting the graft. Typically, the method of anchoring a graft to bone is dependent upon whether the graft is made of soft tissue, such as a hamstring tendon graft, or whether a bone-tendon-bone type graft is used. By way of example, one method for ACL reconstruction uses a bone-tendon-bone graft and an interference screw, which may be inserted into a bone tunnel parallel to the bone block of the bone-tendon-bone graft. According to this method, holes are typically drilled in the bone block for passing sutures, which serve to pull the graft through the tunnel and into place. The bone block is then anchored in the bone tunnel by inserting an interference screw in the tunnel adjacent the bone block. The compressive action of the screw threads against the bone block and tunnel walls is intended to anchor the bone block of the graft in place.

Alternatively, ACL reconstruction may be accomplished with a hamstring tendon graft. This type of graft has also been secured in a bone tunnel with an interference screw. In this situation, an interference screw may be wedged between the soft-tissue graft and the bone tunnel to anchor the end of the graft in the tunnel. Soft tissue graft fixation may alternatively be accomplished by placing a pin transversely through the femoral tunnel and through the loop of a hamstring graft which is doubled over the transverse pin. Fixation using the cross pin involves preparation of a bone tunnel for placement of the graft and an additional, transverse bone tunnel for the transversely oriented pin.

Known devices and methods for installing and anchoring soft tissue and bone-tendon-bone grafts suffer from inadequacies which can result in damage to the graft, excess trauma to the patient receiving the graft, and/or an increase in post-operative recovery time. In particular, many known devices and graft fixation methods do not allow for satisfactory tensioning of the graft. For example, when an interference screw is used to anchor one end of the graft in a bone tunnel, the screw typically must be removed in order to adjust graft tension. Such removal can cause the graft to tear. Further, the use of an interference screw may prevent a portion of a graft and/or a bone block, or bone anchor, from contacting with the bone tunnel, which may slow the healing process.

SUMMARY OF THE INVENTION

According to one aspect of the invention, there is provided a bone block assembly, the assembly including a bone block having a proximal end, a distal end, a central axis defined therethrough, and a hole formed therethrough, and a threaded screw having a proximal end, a distal end, and a first eyelet formed on the proximal end of the threaded screw, the threaded screw configured to be received within the hole of the bone block, in which the first eyelet of the threaded screw is, at least partially, exposed on the proximal end of the bone block when the threaded screw is fully engaged with the bone block, and in which the first eyelet of the threaded screw is configured to receive a suture.

According to another aspect of the invention, there is provided a method of preparing a bone block assembly for surgery, the method including providing a bone block having a central axis defined therethrough, and disposing a threaded screw into the bone block, the threaded screw having a first eyelet formed on a proximal end of the threaded screw, in which the first eyelet of the threaded screw is configured to receive a suture.

According to another aspect of the invention, there is provided a method of delivering a bone block assembly into a body, the method including providing a bone block having a central axis defined therethrough, the bone block having a threaded screw disposed therein along an axis that is divergent from the central axis of the bone block, the threaded screw having a first eyelet formed on a proximal end of the threaded screw and a suture disposed through the first eyelet of the threaded screw, forming a tunnel through a bone in a body, and suspending the bone block within the tunnel formed through the bone with the suture.

According to another aspect of the invention, there is provided a fixation assembly, the fixation assembly including an anchor member having a hole formed therethrough, an elongate member having an eyelet formed thereon, and a loop of material coupled to the eyelet formed on the elongate member.

According to another aspect of the invention, there is provided a method of securing a fixation assembly within a body, the method including providing an anchor member having a hole formed therethrough, securing an elongate member having an eyelet formed thereon within the hole formed through the anchor member, in which a loop of material is coupled to the eyelet formed on the elongate member, and securing the anchor member within a bone.

BRIEF DESCRIPTION OF THE DRAWINGS

The FIGS. 1A-1B show multiple views of a bone block assembly, according to embodiments disclosed herein.

FIGS. 3A-3D show multiple views of a threaded screw, according to embodiments disclosed herein.

FIG. 7 is a cross-sectional view of an anchor member, according to embodiments disclosed herein.

FIG. 8 is a cross-sectional view of an elongate member, according to embodiments disclosed herein.

FIG. 9 is a side view of a loop of material, according to embodiments disclosed herein.

FIG. 10 is a cross-sectional view of a driving tool, according to embodiments disclosed herein.

DETAILED DESCRIPTION

Figure 1A:
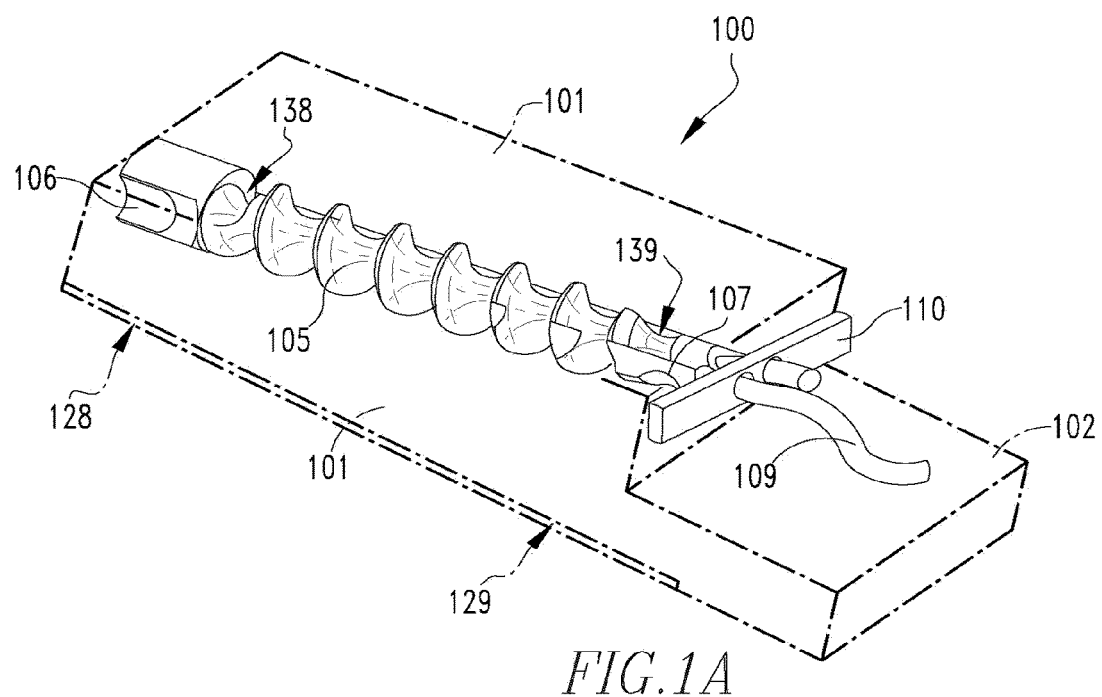
Figure 1B:
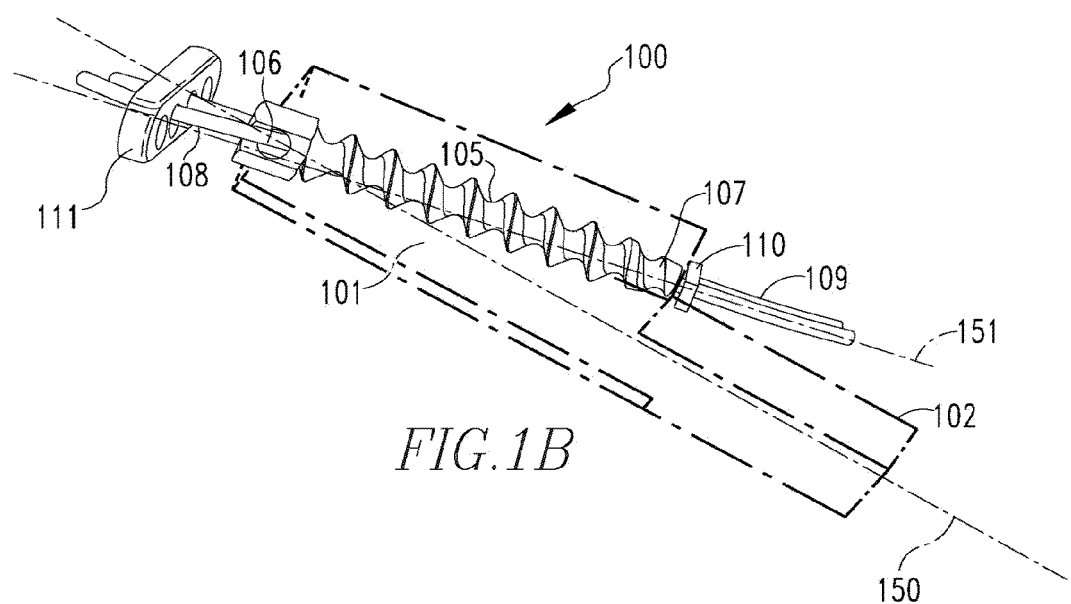

Referring to FIGS. 1A-1B, multiple views of a bone block assembly 100, in accordance with embodiments disclosed herein, are shown. In one or more embodiments, the bone block assembly 100 may include a bone block 101 having a proximal end 128, a distal end 129, a central axis 150 defined therethrough, and a hole (not shown) formed therethrough, and a threaded screw 105 having a proximal end 138, a distal end 139, and a first eyelet 106 formed on the proximal end 138 of the threaded screw 105, in which the threaded screw 105 is configured to be received within the hole of the bone block 101.

As shown, the threaded screw 105 is disposed within, or engaged with, the bone block 101. In one or more embodiments, the first eyelet 106 of the threaded screw 105 may be, at least partially, exposed on the proximal end 128 when the threaded screw 105 is fully engaged with, or disposed within, the bone block 101. Alternatively, in one or more embodiments, the first eyelet 106 of the threaded screw 105 may not necessarily be exposed on the proximal end 128 when the threaded screw 105 is fully engaged with, or disposed within, the bone block 101.

In one or more embodiments, the first eyelet 106 of the threaded screw 105 may be configured to receive a suture 108. Those having ordinary skill in the art will appreciate that the suture 108 may be formed from any material known in the art. For example, the suture 108 may be formed from a biocompatible polyester, plastic, or polyester closure tape and may be, for example, a single or double-arm 2-0 braided non-absorbable polyester suture.

In one or more embodiments, at least one graft 102 may be coupled to the bone block 101. Those having ordinary skill in the art will appreciate that the at least one graft 102 may be any type of graft that may be used in a surgical procedure, including tendons, ligaments, and tissues. Further, those having ordinary skill in the art will appreciate that more than one graft 102 may be coupled to the bone block 101. For example, two, three, four, or more grafts, e.g., graft 102, may be coupled to the bone block 101. Those having ordinary skill in the art will appreciate that the at least one graft 102 may be coupled to the bone block 101 by any means in the art. For example, in one or more embodiments, the bone block 101 may be harvested from another body, in which the at least one graft 102 is already attached, naturally, to the bone block 101.

Still referring to FIGS. 1A-1B, in one or more embodiments, the hole of the bone block 101 may be formed along an axis 151 that may be divergent from the central axis 150 of the bone block 101. In other words, in one or more embodiments, the hole of the bone block 101 may be formed in a direction that is not parallel to the central axis 150 of the bone block 101. For example, as shown in FIG. 1B, the hole of the bone block 101 may be formed along the axis 151, which is not parallel to the central axis 150 of the bone block 101, which may intersect the central axis 150 of the bone block 101. Alternatively, in one or more embodiments, the hole of the bone block 101 may be formed along the central axis 150 of the bone block 101 or in a direction that is substantially parallel to the central axis 150 of the bone block 101.

Further, in one or more embodiments, the threaded screw 105 may include a second eyelet 107 formed on the distal end 139 of the threaded screw 105. In one or more embodiments, the second eyelet 107 of the threaded screw 105 may be configured to receive a suture 109. As discussed above with regard to the suture 108, those having ordinary skill in the art will appreciate that the suture 109 may be formed from any material known in the art. For example, the suture 109 may be formed from a biocompatible polyester, plastic, or polyester closure tape and may be, for example, a single or double-arm 2-0 braided non-absorbable polyester suture. Those having ordinary skill in the art will appreciate that the suture 108 and the suture 109 may be identical sutures. Alternatively, in one or more embodiments, each of the suture 108 and the suture 109 may be different sutures, e.g., different in thickness and/or in length. Furthermore, as will be discussed in further detail below, in one or more embodiments, the threaded screw 105 may be cannulated.

In one or more embodiments, the bone block assembly 100 may include an augmentation bar 110 having at least one hole formed therein. In one or more embodiments, the at least one hole of the augmentation bar 110 may be configured to receive the suture 109. As shown in FIGS. 1A-1B, the suture 109 may be disposed, or looped, through the second eyelet 107 of the threaded screw 105 and may be disposed, or looped, through the at least one hole of the augmentation bar 110.

In one or more embodiments, the augmentation bar 110 may be used to support at least a portion of the bone block 101. For example, referring to FIG. 1B, a knot (not shown) may be tied with the suture 109, which may secure the augmentation bar 110 on, or along, the suture 109. As such, as the bone block 101 may be suspended by the suture 108, threaded through the first eyelet 106 of the threaded screw 105, the augmentation bar 110 may support a distal surface of the bone block 101, in the event that the threaded screw 105 may slip within the bone block 101, e.g., within the hole formed within the bone block 101 in which the threaded screw 105 is disposed. In other words, if a force, e.g., a tensile force on the at least one graft 102, may force the bone block 101 in a direction that is away from the suture 108, the augmentation bar 110 may assist in supporting the bone block 101 against this force, along with the threads of the threaded screw 105. As will be discussed in further detail below, in one or more embodiments, the threaded screw 105 may include self-tapping threads that are configured to form threads in the bone block 101, e.g., threads within the hole formed in the bone block 101 in which the threaded screw 105 is disposed.

In one or more embodiments, the bone block assembly 100 may also include a fixation device 111 configured to suspend the bone block 101 and the at least one graft 102 coupled thereto by a suture 108 by engaging against a surface of a bone. For example, the fixation device 111 may have at least one hole formed therethrough, configured to receive a suture, e.g., the suture 108. In one or more embodiments, the fixation device 111 may have two holes formed therethrough, such that the suture 108 may be looped through the fixation device 111, e.g., passed through the fixation device 111 twice. Alternatively, the fixation device 111 may have three, four, or more holes formed therethrough, which may be configured to receive one or more sutures (not shown), which may be used to re-orient or manipulate the fixation device 111, e.g., within a bone tunnel and/or on the surface of a bone (not shown).

Those having ordinary skill in the art will appreciate that the fixation device 111 may be formed from any material known in the art. For example, in one or more embodiments, the fixation device 111 may be formed from any substantially rigid, biocompatible material known in the art. In one or more embodiments, the fixation device 111 may be formed from stainless steel.

Figure 2A:
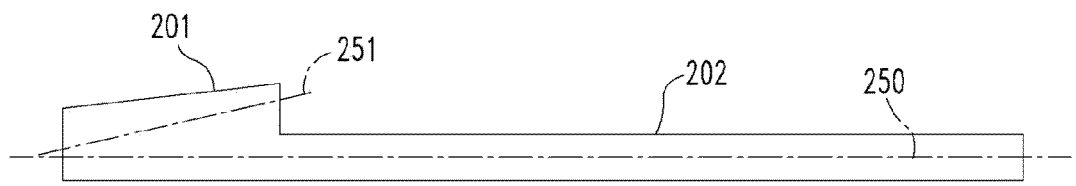
FIGS. 2A-2F show multiple views of a bone block having a hole formed therethrough, according to embodiments disclosed herein.
Figure 2B:
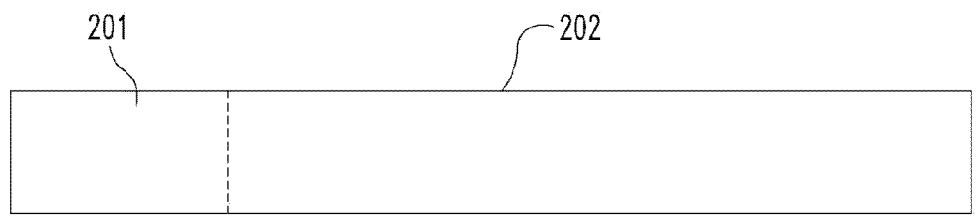
Figure 2C:
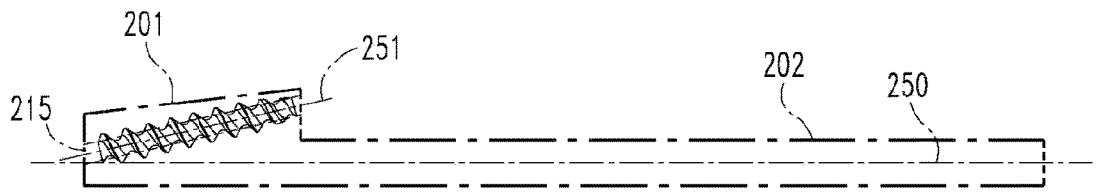

Referring to FIGS. 2A-2F, multiple views of a bone block 201 having a hole 215 formed therethrough, in accordance with embodiments disclosed herein, are shown. In one or more embodiments, the bone block 201 may have a central axis 250 defined therethrough. In one or more embodiments, the hole 215 may be formed along an axis 251 that may be divergent from the central axis 250 of the bone block 201. In other words, in one or more embodiments, the hole 215 of the bone block 201 may be formed in a direction that is not parallel to the central axis 250 of the bone block 201. For example, as shown in FIG. 2C, the hole 215 of the bone block 201 may be formed along the axis 251, which is not parallel to the central axis 250 of the bone block 201, which may intersect the central axis 250 of the bone block 201. Alternatively, in one or more embodiments, the hole 215 of the bone block 201 may be formed along the central axis 250 of the bone block 201 or in a direction that is substantially parallel to the central axis 250 of the bone block 201.

As shown, in one or more embodiments, a cross-section of the bone block 201 may be trapezoidal in shape. In other words, in one or more embodiments, the bone block 201 may have a trapezoidal profile. However, those having ordinary skill in the art will appreciate that the bone block 201 may be formed in any shape known in the art. For example, the bone block 201 may be rectangular, cylindrical, prismatic, or pyramidal in shape. Accordingly, in one or more embodiments, a cross-section of the bone block 201 may be rectangular, elliptical, triangular, or any other shape known in the art.

As discussed above, at least one graft 202 may be coupled to the bone block 201. Those having ordinary skill in the art will appreciate that the at least one graft 202 may be any type of graft that may be used in a surgical procedure, including tendons, ligaments, and tissues. Further, those having ordinary skill in the art will appreciate that more than one graft 202 may be coupled to the bone block 201. For example, two, three, four, or more grafts, e.g., graft 202, may be coupled to the bone block 201. Those having ordinary skill in the art will appreciate that the at least one graft 202 may be coupled to the bone block 201 by any means in the art. For example, in one or more embodiments, the bone block 201 may be harvested from another body, in which the at least one graft 202 is already attached, naturally, to the bone block 201.

Figure 2D:
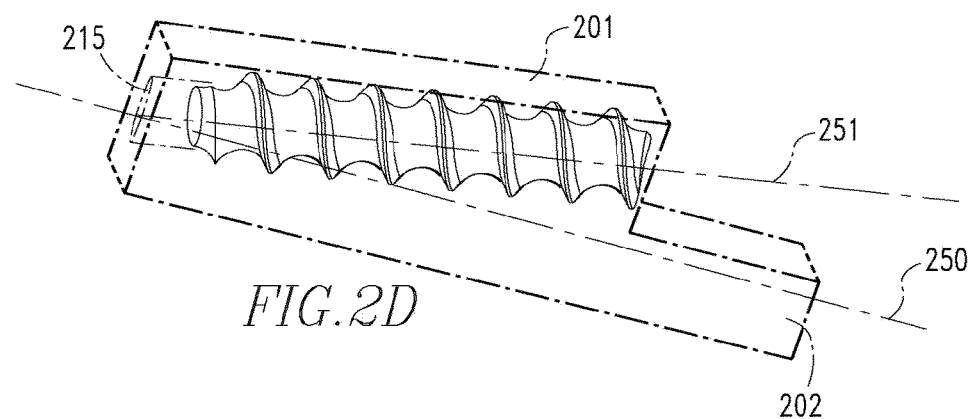
Figure 2E:
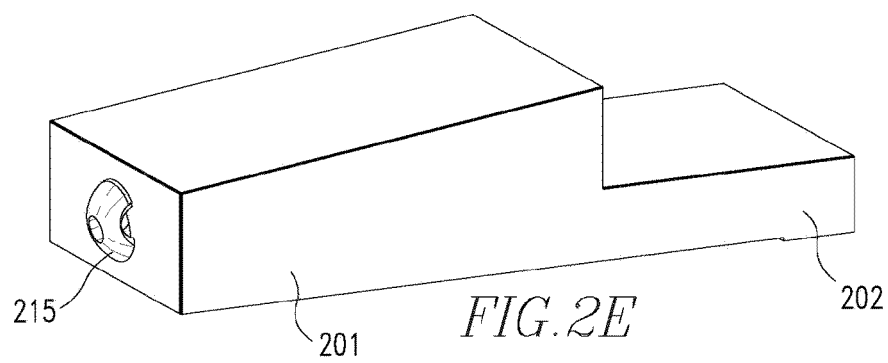
Figure 2F:
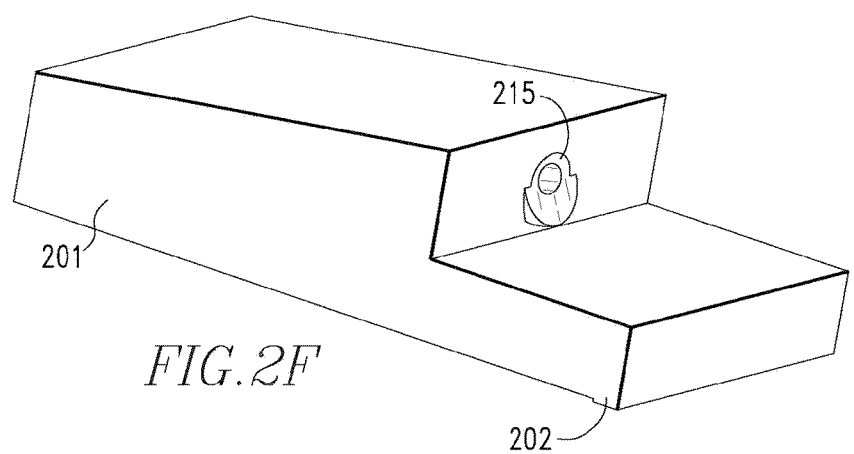

As shown in FIGS. 2C-2D, the hole 215 formed in the bone block 201 may be a threaded hole. For example, the threads formed in the hole 215, which may be configured to engage with a threaded screw, e.g., the threaded screw 105 of FIGS. 1A-1B, may be formed before the threaded screw is engaged with the hole 215. Alternatively, the threaded screw may be a self-tapping screw configured to form threads within the bone block 201, e.g., within the hole 215 formed in the bone block 201. In other words, the hole 215 may be formed in the bone block 201 without threads formed therein, before the threaded screw is engaged with the hole 215. For example, in one or more embodiments, the hole 215 may be a smooth hole, without threads formed therein.

Referring to FIGS. 3A-3D, multiple views of a threaded screw 305, in accordance with embodiments disclosed herein, are shown. In one or more embodiments, the threaded screw 305 may include a proximal end 338, a distal end 339, threads 319 formed on a surface of the threaded screw 305, and a first eyelet 306 formed on the proximal end 338 of the threaded screw 305. As discussed above, the first eyelet 306 may be configured to receive a suture (not shown). Alternatively, in one or more embodiments, the first eyelet 306 may be formed on the distal end 339 of the threaded screw 305. In one or more embodiments, the threads 319 may not be pointed, and may provide for capture of a cortical layer at a bony-ligament junction of the graft. Further, in one or more embodiments, one or more ends of the threaded screw 305 may be configured to engage with a driving tool, as will be discussed below.

In one or more embodiments, the threaded screw 305 may be cannulated. In other words, in one or more embodiments, a hole 320 may be formed through the threaded screw 305. In one or more embodiments, the hole 320 may be configured to receive a surgical tool. Those having ordinary skill in the art will appreciate that the hole 320 may be configured to receive any surgical tool in the art. For example, the hole 320 of the threaded screw 305 may be configured to receive a drilling tool or device, a guide wire, or any other surgical tool known in the art. In one or more embodiments, the hole 320 may be formed through the entire threaded screw 305. Alternatively, in one or more embodiments, the hole 320 may not necessarily be formed through the entire threaded screw 305. For example, in one or more embodiments, the hole 320 of the threaded screw 305 may be formed only partially through the threaded screw 305.

In one or more embodiments, the threads 319 of the threaded screw 305 may be self-tapping threads. In other words, the threads 319 of the threaded screw 305 may be configured to form threads within a body in which the threaded screw 305 is received, e.g., a bone block. Alternatively, the threaded screw 305 may not necessarily be a self-tapping screw. In other words, the threads 319 of the threaded screw 305 may not necessarily be configured to form threads within a body in which the threaded screw 305 is received. For example, a hole formed within a body, e.g., the hole 215 of FIGS. 2C-2D, may be formed with threads configured to engage with the threaded screw 305.

Those having ordinary skill in the art will appreciate that the threaded screw 305 may be formed from any material known in the art. For example, in one or more embodiments, the threaded screw 305 may be formed from any substantially rigid, biocompatible material known in the art. In one or more embodiments, the threaded screw 305 may be formed from stainless steel.

Figure 4A:
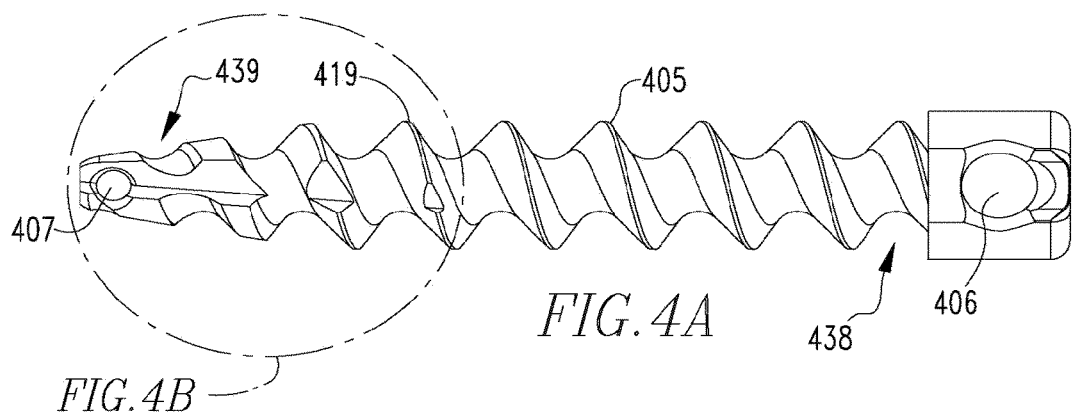
FIGS. 4A-4B show multiple views of another embodiment of a threaded screw, according to embodiments disclosed herein.
Figure 4B:
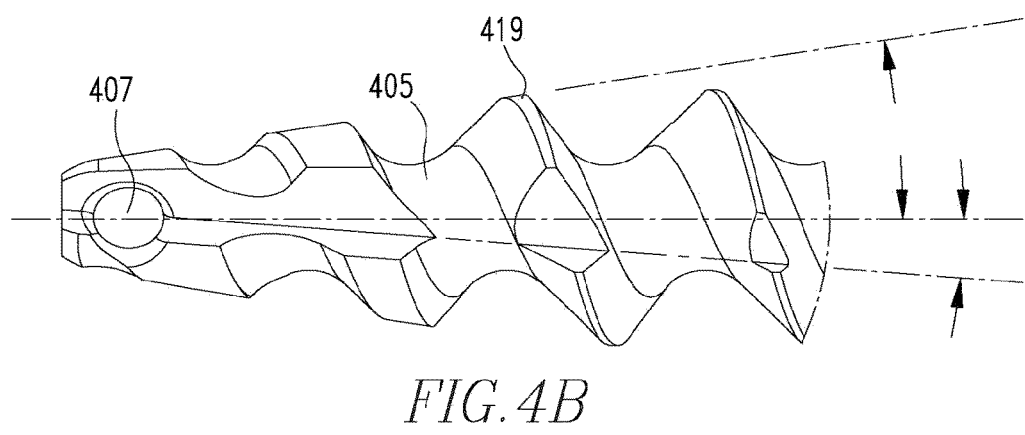

Referring to FIGS. 4A-4B, multiple views of another embodiment of a threaded screw 405, in accordance with embodiments disclosed herein, are shown. In one or more embodiments, the threaded screw 405 may include a proximal end 438, a distal end 439, threads 419 formed on a surface of the threaded screw 405, a first eyelet 406 formed on the proximal end 438 of the threaded screw 405, and a second eyelet 407 formed on the distal end 439 of the threaded screw 405. As discussed above, each of the first eyelet 406 and the second eyelet 407 may be configured to receive a suture (not shown). In one or more embodiments, the threads 419 may not be pointed, and may provide for capture of a cortical layer at a bony-ligament junction of the graft. Further, in one or more embodiments, one or more ends of the threaded screw 405 may be configured to engage with a driving tool, as will be discussed below.

In one or more embodiments, the distal end 439 of the threaded screw 405 may be a tapered end. In other words, as shown in FIGS. 4A-4B, the threaded screw 405 may taper toward the distal end 439 such that a circumference of the distal end 439 may be smaller than a circumference of the proximal end 438. Alternatively, in one or more embodiments, the proximal end 438 may be a tapered end. Alternatively, in one or more embodiments, neither the proximal end 438 or the distal end 439 may be a tapered end. In other words, in one or more embodiments, a circumference, or a cross-section, of the threaded screw 405 may be constant throughout the length of the threaded screw 405. Furthermore, in one or more embodiments, both the proximal end 438 and the distal end 439 may both be tapered ends, in which a circumference of a portion of the threaded screw 405 between the proximal end 438 and the distal end 439 may be larger than a circumference of either the proximal end 438 or the distal end 439. In one or more embodiments, one or more ends of the threaded screw 405 may be tapered, which may assist with forming a hole within a body, e.g., a bone block. For example, in one or more embodiments, each of the proximal end 438 and the distal end 439 may be tapered to a point (not shown), which may assist with forming a hole within a bone block.

In one or more embodiments, the threads 419 of the threaded screw 405 may be self-tapping threads. In other words, the threads 419 of the threaded screw 405 may be configured to form threads within a body in which the threaded screw 405 is received, e.g., a bone block. Alternatively, the threaded screw 405 may not necessarily be a self-tapping screw. In other words, the threads 419 of the threaded screw 405 may not necessarily be configured to form threads within a body in which the threaded screw 405 is received. For example, a hole formed within a body, e.g., the hole 215 of FIGS. 2C-2D, may be formed with threads configured to engage with the threaded screw 405.

Those having ordinary skill in the art will appreciate that the threaded screw 405 may be formed from any material known in the art. For example, in one or more embodiments, the threaded screw 405 may be formed from any substantially rigid, biocompatible material known in the art. In one or more embodiments, the threaded screw 405 may be formed from stainless steel.

Figure 5A:
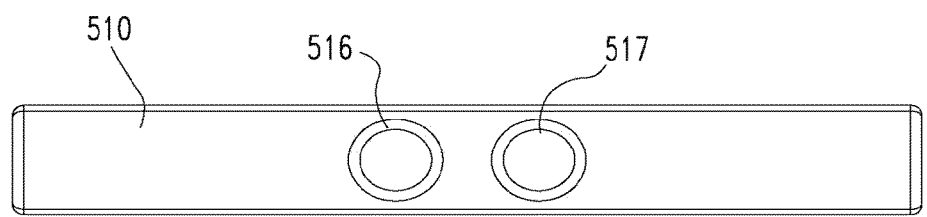
FIGS. 5A-5B show multiple views of an augmentation bar, according to embodiments disclosed herein.
Figure 5B:
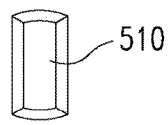

Referring to FIGS. 5A-5B, multiple views of an augmentation bar 510, in accordance with embodiments disclosed herein, are shown. In one or more embodiments, the augmentation bar 510 may include a first hole 516 and a second hole 517 formed therethrough. In one or more embodiments, each of the first hole 516 and the second hole 517 may be configured to receive a suture (not shown). The suture may be threaded, disposed, or looped, through each of the first hole 516 and the second hole 517. Further, the suture may be knotted to prevent the augmentation bar 510 from displacing beyond the knot formed by the suture and may provide support for a bone block, e.g., the bone block 101 of FIGS. 1A-1B, without strangulation.

The augmentation bar 510 may be formed from any material known in the art. For example, in one or more embodiments, the augmentation bar 510 may be formed from any substantially rigid, biocompatible material known in the art. In one or more embodiments, the augmentation bar 510 may be formed from stainless steel.

Figure 6:
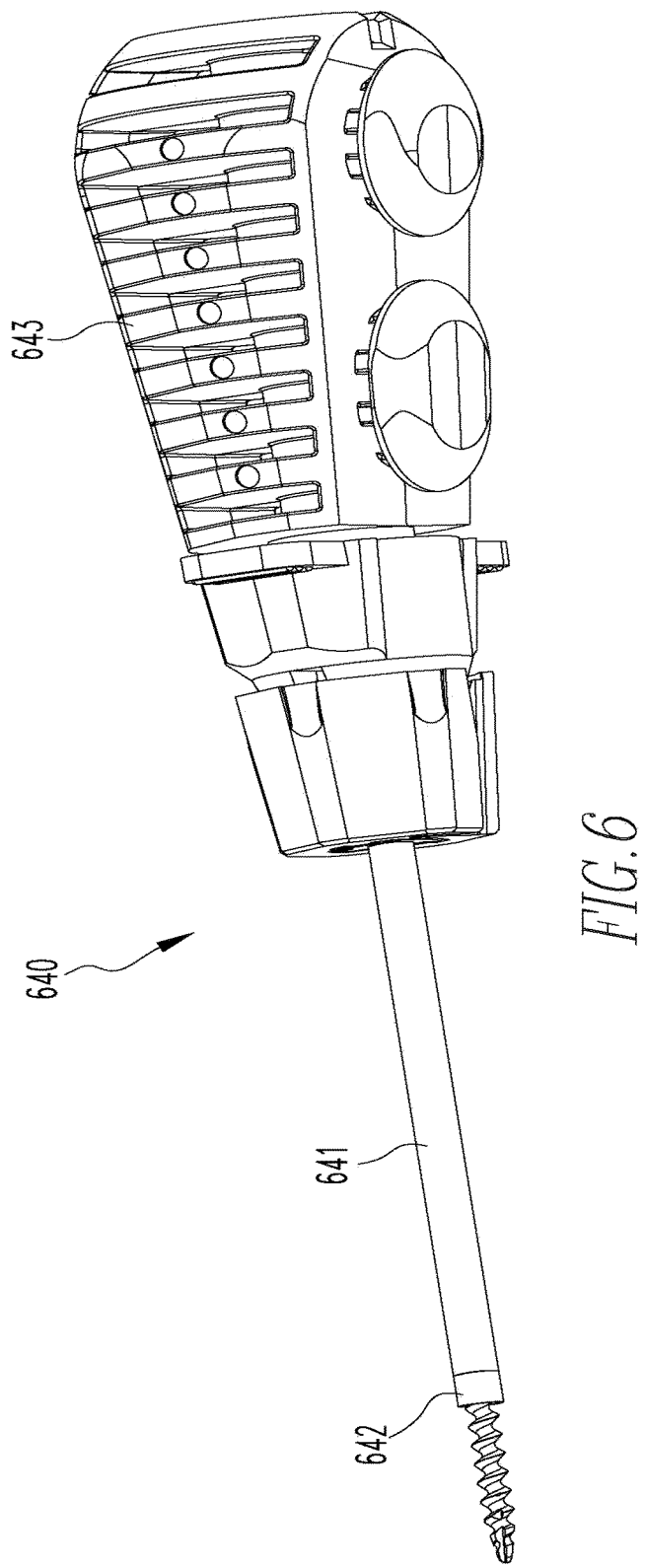
FIG. 6 shows a perspective view of a driving tool, according to embodiments disclosed herein.

Referring to FIG. 6, a perspective view of a driving tool 640, in accordance with embodiments disclosed herein, is shown. In one or more embodiments, the driving tool may include a shaft 641, an engagement tip 642 and a handle 643. In one or more embodiments, the engagement tip 642 may be configured to engage with either a proximal end or a distal end of a threaded screw (not shown). In one or more embodiments, once the engagement tip 642 is engaged with the threaded screw, a surgeon may use the driving tool 640 to drive, dispose, or thread the threaded screw into a body, e.g., the bone block 101 of FIGS. 1A-1B. For example, in one or more embodiments, the surgeon may twist the handle 643 of the driving tool 640 to thread the threaded screw into the bone block. Alternatively, the surgeon may push the threaded screw into the bone block with the driving tool 640. Those having ordinary skill in the art will appreciate that a driving tool, e.g., the driving tool 640 may not be required to engage the threaded screw within the bone block. For example, the threaded screw may be disposed within, or engaged with, the bone block manually.

According to another aspect, there is provided a method of preparing a bone block assembly for surgery. The method may include providing a bone block having a central axis defined therethrough, and disposing a threaded screw into the bone block, the threaded screw having a first eyelet formed on a proximal end of the threaded screw, in which the first eyelet of the threaded screw may be configured to receive a suture. For example, referring back to FIGS. 1A-1B, the bone block 101 may have the central axis 150 defined therethrough. The threaded screw 105, having a first eyelet 106 formed on the proximal end 138 of the threaded screw 105, may be disposed within the bone block 101. As discussed above, the first eyelet 106 may be configured to receive a suture.

According to one or more aspects, disposing the threaded screw into the bone block may include disposing the threaded screw into the bone block along an axis that is divergent from the central axis of the bone block. For example, as shown in FIGS. 1A-1B, the threaded screw 105 may be disposed into the bone block 105 along an axis 151 that is divergent from the central axis 150 of the bone block 105. In other words, according to one or more aspects, the hole of the bone block 101, in which the threaded screw 105 is disposed, may be formed in a direction that is not parallel to the central axis 150 of the bone block 101. For example, as shown in FIG. 1B, the hole of the bone block 101 may be formed along the axis 151, which is not parallel to the central axis 150 of the bone block 101, which may intersect the central axis 150 of the bone block 101. Alternatively, according to one or more aspects, the hole of the bone block 101 may be formed along the central axis 150 of the bone block 101 or in a direction that is substantially parallel to the central axis 150 of the bone block 101.

Further, according to one or more aspects, the first eyelet of the threaded screw may be, at least partially, exposed on a proximal end of the bone block when the threaded screw is fully disposed within the bone block. For example, as shown in FIG. 1B, the first eyelet 106 formed on the proximal end of the threaded screw 105 may be, at least partially, exposed on the proximal end of the bone block 101 when the threaded screw 105 is fully disposed within, or engaged with, the bone block 101. This may allow a suture, e.g., the suture 108, that may be disposed through the first eyelet 106 to extend from the bone block 101. In other words, at least partially exposing the first eyelet 106 on the proximal end of the bone block 101 may allow the bone block 101 to be suspended from the suture 108.

However, those having ordinary skill in the art will appreciate that the first eyelet 106 formed on the proximal end of the threaded screw 105 may not necessarily need to be, at least partially, exposed on the proximal end of the bone block 101 when the threaded screw 105 is fully disposed within, or engaged with, the bone block 101. For example, according to one or more aspects, the suture 108 may still extend from the proximal end of the bone block 101, though the first eyelet 106 of the threaded screw 105 may be completely disposed within the bone block 101.

Furthermore, according to one or more aspects, at least one graft may be coupled to the bone block. Those having ordinary skill in the art will appreciate that the at least one graft may be any type of graft that may be used in a surgical procedure, including tendons, ligaments, and tissues. Further, those having ordinary skill in the art will appreciate that more than one graft may be coupled to the bone block. For example, referring back to FIGS. 1A-1B, two, three, four, or more grafts, e.g., the at least one graft 102, may be coupled to the bone block 101. Those having ordinary skill in the art will appreciate that the at least one graft 102 may be coupled to the bone block 101 by any means in the art. For example, in one or more embodiments, the bone block 101 may be harvested from another body, in which the at least one graft 102 is already attached, naturally, to the bone block 101.

The method may also include disposing a suture through the first eyelet of the threaded screw. For example, referring to FIGS. 1A-1B, the suture 108 may be threaded, looped, or disposed through the first eyelet 106 of the threaded screw 105, which is engaged with the bone block 101. Accordingly, the bone block 101 with the at least one graft 102 coupled thereto, may be suspended by the at least one suture 108, e.g., suspended within a bone tunnel.

According to another aspect, there is provided a method of delivering a bone block assembly into a body. The method may include providing a bone block having a central axis defined therethrough, the bone block having a threaded screw disposed therein, the threaded screw having a first eyelet formed on a proximal end of the threaded screw and a suture disposed through the first eyelet of the threaded screw, forming a tunnel through a bone in a body, and suspending the bone block within the tunnel formed through the bone with the suture.

For example, referring back to FIGS. 1A-1B, the bone block 101 may have the central axis 150 defined therethrough and the threaded screw 105 disposed therein, the threaded screw 105 having the first eyelet 106 formed on the proximal end 138 of the threaded screw 105 and the suture 108 disposed through the first eyelet 106 of the threaded screw 105.

Further, a tunnel (not shown) may be formed through a bone (not shown) in a body (not shown). For example, a medial portal incision may be made to access a femur and a tunnel may be created from either inside the joint space or from outside the joint space. This tunnel may be formed by any means known in the art. For example, one or more guidewires may be disposed into the bone, and cannulated drills may be used to drill the tunnel over the guidewires. Alternatively, an initial tunnel may be drilled into the bone, e.g., a femur or a tibia, and a bone dilator may be used to form the tunnel from the initial tunnel. Alternatively, a drilling device may be used to form the tunnel within the bone. Those having ordinary skill in the art will appreciate that the tunnel may be constant in diameter, or may be variable in diameter. Further, those having ordinary skill in the art will appreciate that the tunnel may be formed in any shape known in the art. For example, the tunnel may be circular, elliptical, rectangular, or any other shape known in the art. Furthermore, those having ordinary skill in the art will appreciate that the tunnel may be formed in any bone in a body and may not be limited to the femur and the tibia.

An implant, e.g., the bone block assembly 100, may be disposed within the tunnel formed in the bone and the bone block assembly 100 may be suspended within the tunnel with the suture, e.g., the suture 108. Suspension of the bone block assembly 100 within the bone tunnel, without the use of an interference screw, cross pins, or other suspensory devices, may promote maximum contact between the bone block 101 and the bone wall of the tunnel. Further, according to one or more aspects, the bone block 101 may be shaped, specifically, to promote this type of contact, while still allowing for tension to be applied to the suture 108 suspending the bone block 101 within the tunnel, without allowing the bone block 101 to be pulled completely through the tunnel 101.

According to one or more aspects, the threaded screw may be disposed within the bone block along an axis that is divergent from the central axis of the bone block. For example, as shown in FIGS. 1A-1B, the threaded screw 105 may be disposed into the bone block 105 along an axis 151 that is divergent from the central axis 150 of the bone block 105. In other words, according to one or more aspects, the hole of the bone block 101, in which the threaded screw 105 is disposed, may be formed in a direction that is not parallel to the central axis 150 of the bone block 101. For example, as shown in FIG. 1B, the hole of the bone block 101 may be formed along the axis 151, which is not parallel to the central axis 150 of the bone block 101, which may intersect the central axis 150 of the bone block 101. Alternatively, according to one or more aspects, the hole of the bone block 101 may be formed along the central axis 150 of the bone block 101 or in a direction that is substantially parallel to the central axis 150 of the bone block 101.

According to one or more aspects, at least one graft may be coupled to the bone block. Those having ordinary skill in the art will appreciate that the at least one graft may be any type of graft that may be used in a surgical procedure, including tendons, ligaments, and tissues. Further, those having ordinary skill in the art will appreciate that more than one graft may be coupled to the bone block. For example, referring back to FIGS. 1A-1B, two, three, four, or more grafts, e.g., the at least one graft 102, may be coupled to the bone block 101. Those having ordinary skill in the art will appreciate that the at least one graft 102 may be coupled to the bone block 101 by any means in the art. For example, in one or more embodiments, the bone block 101 may be harvested from another body, in which the at least one graft 102 is already attached, naturally, to the bone block 101.

According to one or more aspects, the method may also include disposing the suture into the tunnel formed through the bone, and pulling the bone block into the tunnel by the suture.

For example, referring back to FIGS. 1A-1B, the tunnel formed in the bone may be tapered, and a profile of the bone block 101 of the bone block assembly 100 may be substantially trapezoidal in shape, or wedge, shaped, in which the profile of the bone block 101 is configured to engage with the tunnel formed in the bone. As such, according to one or more aspects, the suture 108 may be disposed into, and through, the tunnel, and the bone block 101 may be drawn into the tunnel using the suture 108. The bone block 101 may engage with the bone wall of the tunnel without the use of an interference screw. Further, the tapered shape of the tunnel, and the wedge-shape of the bone block 101, may prevent the bone block 101 from being pulled completely through the tunnel, despite a tensile force acting on the suture 108, e.g., on the bone block 101.

According to one more aspects, suspending the bone block within the tunnel formed through the bone with the suture may include securing the suture on a surface of the bone.

As discussed above, according to one or more aspects, the bone block assembly 100 may also include a fixation device 111 configured to suspend the bone block 101 and the at least one graft 102 coupled thereto by a suture 108 by engaging against a surface of a bone. According to one or more aspects, the suture 108 may be coupled to the fixation device 111. Further, according to one or more aspects, a width of the fixation device 111 may be larger than a diameter of the tunnel formed in the bone. As such, the bone block 101, which may be suspended within the tunnel by the suture 108, may be suspended by the fixation device 111, which may engage with a surface of the bone on an opposite side of the tunnel.

For example, according to one or more aspects, the suture 108 may be coupled to both the fixation device 111 and the threaded screw, which is engaged with the bone block 101. The suture 108 and the fixation device may be disposed into a first end of a tunnel formed in a bone, and may exit a second end of the tunnel formed in the bone. The suture 108 may be tensioned from the second end of the tunnel until the bone block 101 is adequately engaged within the tunnel, e.g., adequate engagement between the bone block 101 and the bone wall of the tunnel. Subsequently, according to one or more aspects, the fixation device 111 may be oriented on the surface of the bone to prevent the fixation device 111 from displacing back into the tunnel, i.e., suspending the suture 108 and the rest of the bone block assembly 100 within the tunnel.

Advantageously, embodiments disclosed herein may provide a bone block assembly, a method of preparing a bone block assembly for surgery, and a method of delivering a bone block assembly into a body without the use of an interference screw. As such, aspects discussed to herein may allow for 360 degrees of healing in cruciate reconstruction. Such types of ACL re-construction, involving the bone block assembly and methods discussed herein, may provide unhampered bone wall contact between a bone block/plug and a tunnel formed in a bone for optimal strength and healing. As such, this may improve the overall recovery process following a surgical procedure.

According to yet another aspect, there is provided a fixation assembly that may be used for cruciate reconstruction. Referring to FIGS. 7-10, various components of a fixation assembly, according to embodiments disclosed herein, are shown.

Referring to FIG. 7, an anchor member 763, according to embodiments disclosed herein, is shown. In one or more embodiments, the anchor member 763 may have a hole 770 formed therethrough. In one or more embodiments, the hole 770 may be a threaded hole.

Further, in one or more embodiments, an outer surface of the anchor member 763 may be a threaded outer surface that may be configured to be threaded into, e.g., secured within, a hole (not shown) formed in a bone (not shown). In other words, the outer surface of the anchor member 763 may include threads 777 that may be configured to be threaded in a bone. In one or more embodiments, the threads 777 formed on the outer surface of the anchor member 763 may be self-tapping threads. In other words, the hole formed in the bone may be formed without threads formed therein, before the anchor member 763 is disposed, e.g. engaged, therein. For example, in one or more embodiments, the hole formed in the bone may be a smooth hole, without threads formed therein.

However, those having ordinary skill in the art will appreciate that other structural elements, other than threads, may be formed on the outer surface of the anchor member that may also allow the anchor member to be secured within a bone. For example, in one or more embodiments, the outer surface of the anchor member 763 may be a barbed surface (not shown) having a plurality of barbs that may be configured to engage with a bone.

Further, those having ordinary skill in the art will appreciate that the anchor member 763 may be formed from any material known in the art. For example, in one or more embodiments, the anchor member 763 may be formed from any substantially rigid, biocompatible material known in the art. In one or more embodiments, the anchor member 763 may be formed from stainless steel.

In one or more embodiments, the anchor member 763 may include a portion 769 formed within the anchor member 763 that may be configured to engage with an end of a driving tool (not shown), as will be discussed below.

Referring to FIG. 8, an elongate member 862, according to embodiments disclosed herein, is shown. In one or more embodiments, the elongate member 862 may have an eyelet 868 formed thereon. For example, in one or more embodiments, the elongate member 862 may have a proximal end and a distal end and the eyelet 868 may be formed on one of the proximal end or the distal end of the elongate member 862. In one or more embodiments, the eyelet 868 of the elongate member 862 may be configured to receive a loop of material (not shown). In one or more embodiments, a circumference of the eyelet 868 may be greater than an outer diameter of the elongate member 862, e.g., a shaft of the elongate member 862. Alternatively, in one or more embodiments, the circumference of the eyelet 868 may be less than or equal to the outer diameter of the elongate member 862.

In one or more embodiments, the elongate member 862 may include threads formed on an outer surface of the elongate member 862. As discussed above, the anchor member, e.g., the anchor member 763, may have a threaded hole formed therethrough. In one or more embodiments, the threaded outer surface of the elongate member 862 may be configured to engage with the threaded hole of the anchor member. In one or more embodiments, the threads formed on the outer surface of the elongate member may be self-tapping threads. In other words, the hole formed in the anchor member may be formed without threads formed therein, before the elongate member 862 is disposed, e.g. engaged, therein. For example, in one or more embodiments, the hole formed in the anchor member may be a smooth hole, without threads formed therein.

Those having ordinary skill in the art will appreciate that the elongate member 862 may be formed from any material known in the art. For example, in one or more embodiments, the elongate member 862 may be formed from any substantially rigid, biocompatible material known in the art. In one or more embodiments, the elongate member 862 may be formed from stainless steel.

Referring to FIG. 9, a loop of material 964, according to embodiments disclosed herein, is shown. In one or more embodiments, the loop of material 964 may be coupled to an eyelet formed on an elongate member, e.g., the eyelet 868 formed on the elongate member 862. In one or more embodiments, the loop of material 964 may be a closed, continuous loop. In other words, the loop of material 964 may be a closed loop that is not a tied, or knotted, loop. For example, as shown, the loop of material 964 is not knotted. Instead, the loop of material 964 are closed loops that are closed without the use of knots and may be formed onto the eyelet of the elongate member. Alternatively, in one or more embodiments, the loop of material 964 may be a knotted closed loop having one or more knots and may be tied onto the loop of the elongate member.

In one or more embodiments, the loop of material 964 may be configured to be coupled, or attached, to separate grafts, e.g., anteromedial and posterolateral fiber bundles. However, those having ordinary skill in the art will appreciate that the loop of material 964 may be configured to be coupled, or attached, to any other grafts known in the art.

In one or more embodiments, the loop of material 964 may be formed from a substantially soft material. Alternatively, in one or more embodiments, the loop of material 964 may be formed from a substantially hard material. Moreover, in one or more embodiments, the loop of material 964 may be formed from a combination of a substantially soft material and a substantially hard material. The loop of material 964 may be formed from any biocompatible material known in the art. For example, in one or more embodiments, the loop of material 964 may be formed from a continuous loop of polyester, suture, or polyester closure tape. Alternatively, as discussed above, the loop of material 964 may be a knotted, closed loop of material, such as polyester, suture, or polyester closure tape. Furthermore, the dimensions of the loop of material 964, e.g., a length or size of the loop of material 964, may be adapted based on the size or type of graft to be coupled to the loop of material 964.

Referring to FIG. 10, a driving tool 1061, in accordance with embodiments disclosed herein, is shown. In one or more embodiments, the driving tool 1061 may have an end 1066 that may be adapted, or configured, to engage with at least a portion of an anchor member (not shown), e.g., with the portion 769 of the anchor member 763. As the end 1066 of the driving tool 1061 may be engaged with at least a portion of the anchor member, the driving tool may be used, e.g., torqued, to drive the anchor member into a bone (not shown). In other words, the driving tool 1061 may be used to translate a torque and/or a force imposed on the driving tool 1061 into the anchor member, which may assist with securing/engaging the anchor member within the bone.

Those having ordinary skill in the art will appreciate that one or more embodiments of the driving tool 1061 may be coupled to a handle (not shown) and/or any other means of imposing/inducing a force or torque on the driving tool 1061. For example, in one or more embodiments, the driving tool 1061 may be coupled to a powered drill or any other means known in the art that may be used to impose a force or torque on the driving tool 1061.

In one or more embodiments, the driving tool 1061 may be cannulated. In other words, in one or more embodiments, the driving tool 1061 may have a hole 1065 formed therethrough. Further, in one or more embodiments, the hole 1065 formed through the driving tool 1061 may be configured to receive at least a portion of an elongate member (not shown), e.g., the elongate member 862. In other words, in one or more embodiments, a diameter of the hole 1065 of the driving tool 1061 may be substantially equal to, or slightly larger than, the outer diameter of the elongate member 862.

As discussed above, referring to FIGS. 7-10, the elongate member 862 may have a threaded outer surface that may be configured to engage with a hole formed in an anchor member (not shown), e.g., the hole 770 of the anchor member 763. Once the elongate member is engaged with, or secured within, the anchor member, the driving tool 1061 may be disposed over the elongate member and the end 1066 of the driving tool may engage with a portion of the anchor member, e.g., the portion 769 of the anchor member 763, while the elongate member is engaged with the anchor member. In other words, although the elongate member is engaged with the anchor member, and may extend beyond the anchor member, the driving tool 1061 may still be used to engage with the anchor member and may be used to drive, secure, or engage the anchor member within a bone (not shown).

According to another aspect, there is provided a method of securing a fixation assembly within a body, the method including providing an anchor member having a hole formed therethrough, securing an elongate member having an eyelet formed thereon within the hole formed through the anchor member, and securing the anchor member within a bone. In one or more embodiments, a loop of material may be coupled to the eyelet formed on the elongate member.

According to one or more aspects, a lateral incision may be made in a body and a tunnel may be created in a bone either from inside the joint space or from outside the joint space. In one or more embodiments, the bone may be a femur or tibia; however, those having ordinary skill in the art will appreciate that the bone, according to embodiments disclosed herein, may be any bone in the body. Further, those having ordinary skill in the art will appreciate that the tunnel may be formed in the bone using any means known in the art. For example, in one or more embodiments, the tunnel may be formed in the bone using a drill. Alternatively, in one or more embodiments, the tunnel may be formed using guide wires that may be secured in the bone, and drills, dilators, etc. may be used to form a tunnel in the bone.

In one or more embodiments, a graft may be coupled to the loop of material that may be coupled to the eyelet formed on the elongate member. As discussed above, the graft may be anteromedial and posterolateral fiber bundles. However, those having ordinary skill in the art will appreciate that graft(s) that may be coupled to the loop of material may be any other grafts known in the art.

According to one or more aspects, securing the anchor member within the bone may include driving the anchor member into the bone with the driving tool, in which an end of the driving tool is configured to engage with at least a portion of the anchor member.

Figure 11A:
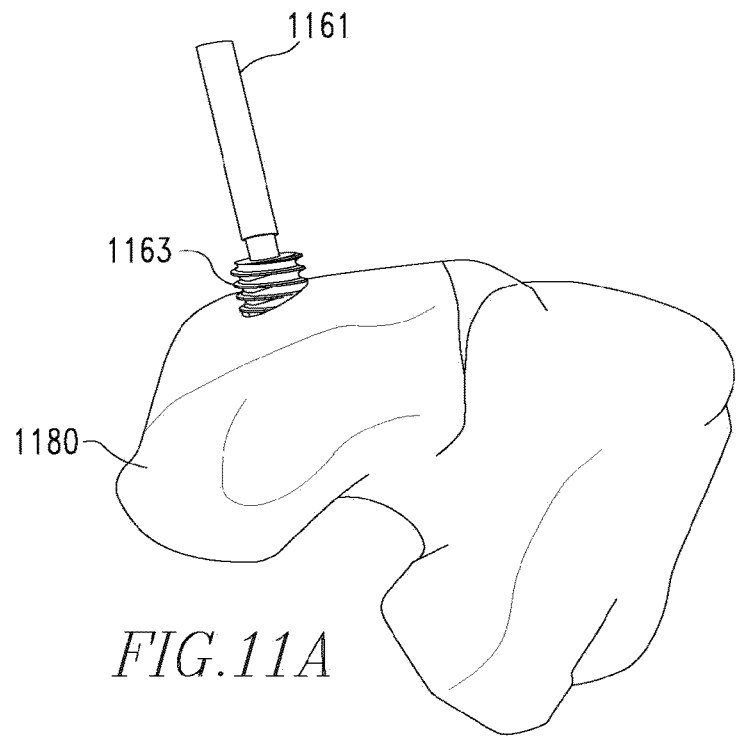
FIGS. 11A-11B are multiple views of securing a fixation assembly within a bone, according to embodiments disclosed herein.
Figure 11B:
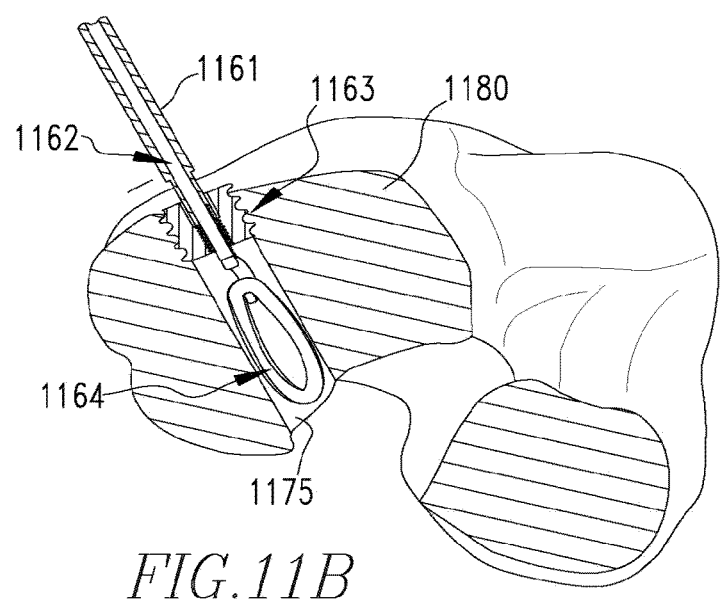

Referring to FIGS. 11A-11B, multiple views of securing a fixation assembly within a bone 1180, according to embodiments disclosed herein, are shown. As discussed above, the fixation assembly, according to embodiments disclosed herein, may include an anchor member 1163, an elongate member 1162, and a loop of material 1164. Further, according to one or more aspects, the fixation assembly may include a driving tool 1161. As shown, the driving tool 1161 may be engaged with the anchor member 1163 and, according to one or more aspects, the driving tool 1161 may be used to drive, secure, or engage the anchor member 1163 into, or within, the bone 1180 to a predetermined depth based on the intended position of a graft (not shown) that may be coupled to the loop of material 1164.

As discussed above, the elongate member 1162 may have a threaded outer surface that may be configured to engage with a hole formed in the anchor member 1163. Once the elongate member 1162 is engaged with, or secured within, the anchor member 1163, the driving tool 1161 may be disposed over the elongate member 1162 and an end of the driving tool 1161 may engage with a portion of the anchor member 1163, e.g., the portion 769 of the anchor member 763 shown in FIG. 7, while the elongate member 1162 is engaged with the anchor member 1163. In other words, although the elongate member 1162 is engaged with the anchor member 1163, and may extend beyond the anchor member 1163, as shown in FIG. 11B, the driving tool 1161, having a hole formed therethrough, may still be used to engage with the anchor member 1163 and may be used to drive, secure, or engage the anchor member 1163 within the bone 1180.

According to one or more aspects, the method may also include severing at least a portion of the elongate member such that the elongate member does not extend beyond the anchor member on at least one end of the anchor member.

Referring to FIGS. 12A-12E, multiple views of a fixation assembly secured within a bone 1280, according to embodiments disclosed herein, are shown. As shown, an elongate member 1262 having a loop of material 1264 coupled thereto is engaged with an anchor member 1263. A tunnel 1275 may be formed within the bone 1280 and the anchor member 1263 may be disposed and secured within the tunnel 1275 using a driving tool (not shown), as discussed above.

Once the anchor member 1263 is engaged within the bone 1280, e.g., within the tunnel 1275 formed in the bone 1280, at least a portion of the elongate member 1262 may be severed such that the elongate member 1262 does not extend beyond the anchor member 1263 on at least one end of the anchor member 1263. In other words, once the anchor member 1263 is engaged within the bone 1280, the driving tool may be removed, e.g., disengaged from the anchor member 1263, and any portion of the elongate member 1262 that may extend beyond the anchor member 1263 may be severed, or cut. That is to say, the elongate member 1262 may be severed such that an end of the elongate member 1262 that is opposite the end of the elongate member having the eyelet formed thereon may be flush with a top surface of the anchor member 1263. According to one or more aspects, the top surface of the anchor member 1263 may be in line with, or flush with, a surface of the bone 1280. Accordingly, according to one or more aspects, one end of the elongate member 1262 may be flush with the surface of the bone 1280, e.g., a femoral cortex.

Figure 12A:
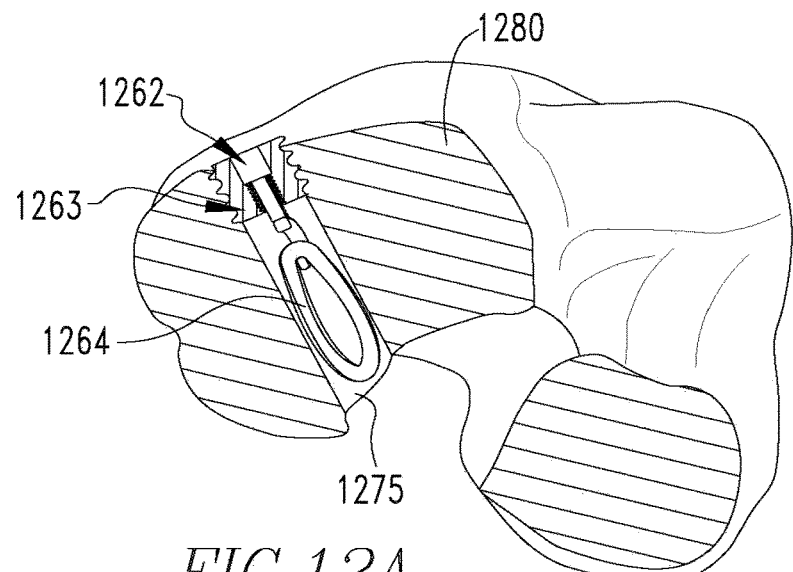
FIGS. 12A-12E are multiple views of a fixation assembly secured within a bone, according to embodiments disclosed herein.
Figure 12B:
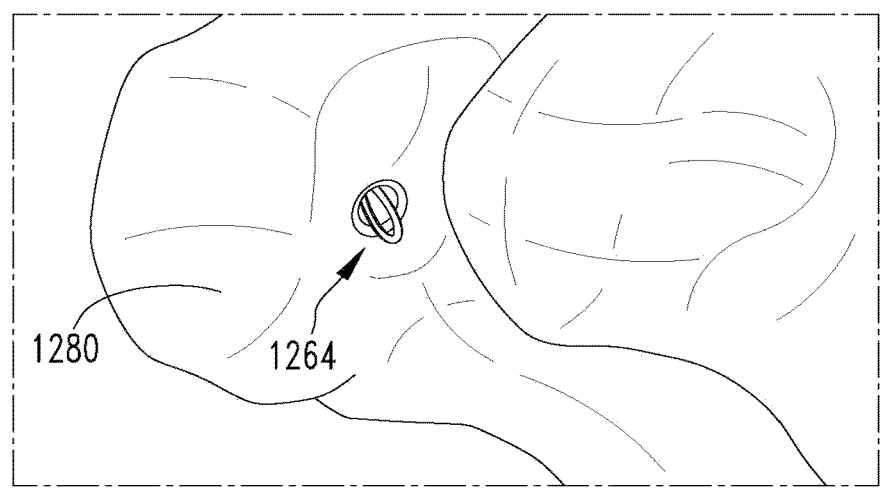
Figure 12C:
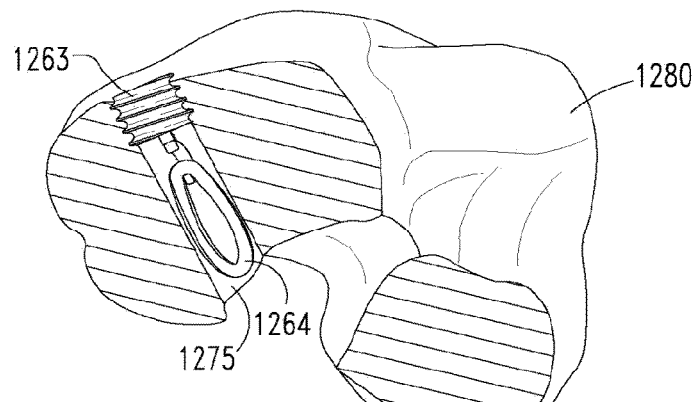
Figure 12D:
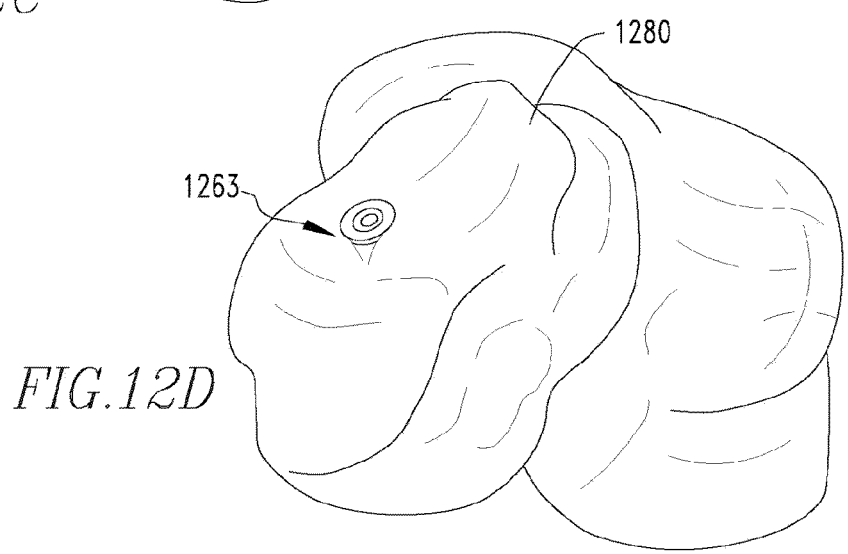
Figure 12E:
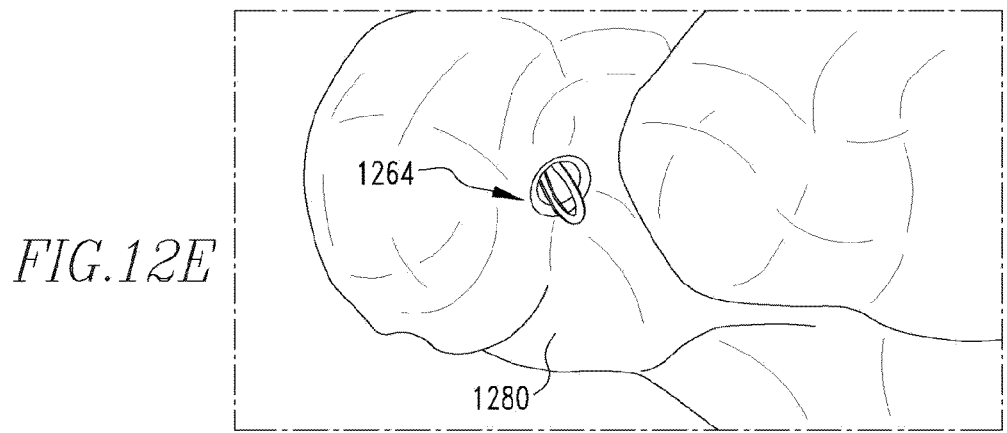

According to one or more aspects, at least a portion of the loop of material may be exposed from the bone. As shown in FIG. 12B, at least a portion of the loop of material 1264 may be exposed from the bone 1280, which may allow a graft (not shown) to be coupled to the loop of material 1264 after the loop of material 1264 is secured within the bone 1280, via the elongate member 1262 and the anchor member 1263, as discussed above. Those having ordinary skill in the art will appreciate that, according to one or more aspects, the graft may be coupled to the loop of material 1264 prior to the elongate member 1262 and the anchor member 1263 being secured within the bone 1280.

Figure 13:
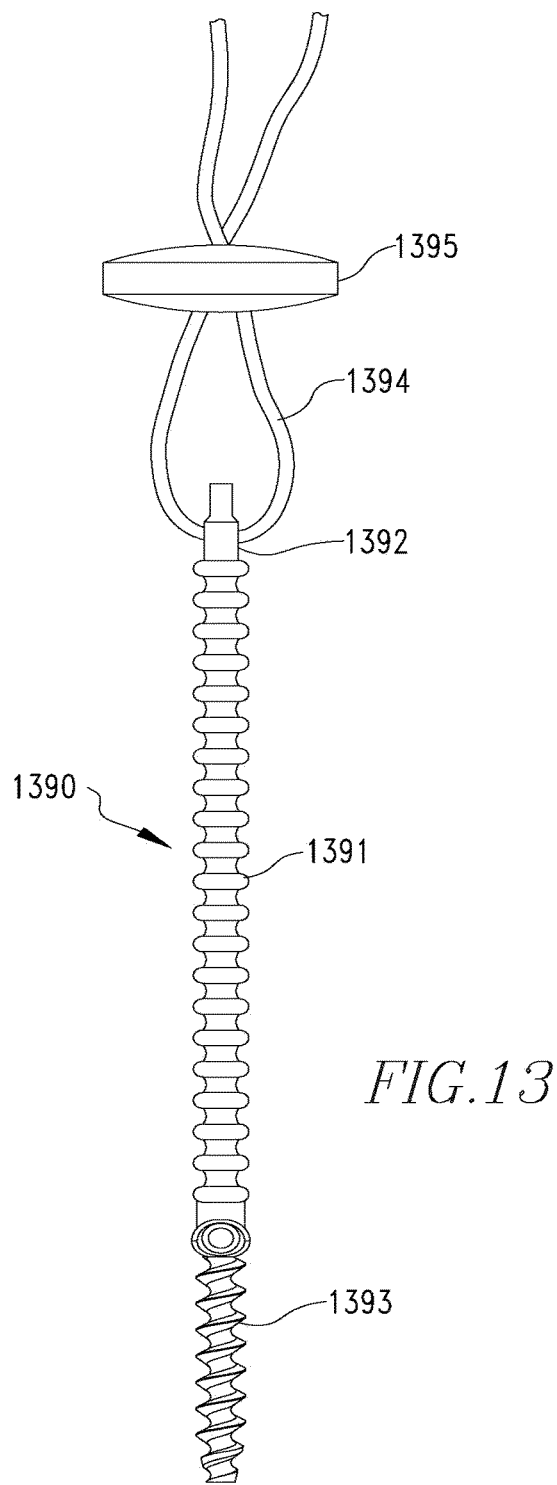
FIG. 13 is a top view of a fixation device, according to embodiments disclosed herein.

Referring to FIG. 13, a fixation device 1390, according to embodiments disclosed herein, is shown. In one or more embodiments, the fixation device 1390 may have a body 1391 having a proximal end 1392 and a distal end 1393. In one or more embodiments, the proximal end 1392 of the body 1391 may have an eyelet formed thereon or a through-hole formed therethrough, in which a suture 1394 may be disposed therethrough. Further, in one or more embodiments, a button 1395 may be coupled to the suture 1394 and may be connected to the body 1391 of the fixation device 1390. Those having ordinary skill in the art will appreciate that the suture 1394 may be formed from polyester, polyester closure tape, or any other suture material known in the art.

In one or more embodiments, the distal end 1392 of the body 1391 of the fixation device 1390 may be a threaded end. In one or more embodiments, the distal end 1392 of the body 1391 may resemble a screw and may have a pointed tip and self-tapping threads.

Further, in one or more embodiments, an outer surface of the body 1391 of the fixation device 1390 may have structural elements that may allow the body 1391 of the fixation device 1390 to be secured within a bone. For example, in one or more embodiments, the outer surface of the body 1391 of the fixation device 1390 may be a threaded surface. Alternatively, the outer surface of the body 1391 of the fixation device 1390 be a barbed surface and may include a plurality of barbs configured to secure the body 1391 of the fixation device 1390 within a bone.

According to one or more aspects, the button 1395 may be rotatably driven or axially driven onto the body 1391 of the fixation device 1390, e.g., into a tunnel formed in a bone. The button 1395 may be driven onto the body 1391 of the fixation device 1390 until the button 1395 rests over the tunnel formed in the bone, e.g., a femur. For example, the button 1395 may be driven onto the body 1391 of the fixation device 1390 until the button 1395 rests over femoral tunnel opening and against a femoral cortex, e.g., an outer surface of the femur. Once the button 1395 is driven to rest over the femoral tunnel opening and against the femoral cortex, a remaining portion of the body 1391 of the fixation device 1390 may be removed.

Advantageously, embodiments disclosed herein may provide a fixation assembly and a method of securing a fixation assembly within a bone that may reduce the amount of movement of reconstructed element within a body. For example, embodiments and aspects disclosed herein may provide anchor members that may be fixed to the cortical surface and provide stability to grafts secured thereto. Further, according to embodiments disclosed herein, the eyelet of the elongate member, which may be coupled to a loop of material and/or directly to a graft, may be adjacent or in close proximity to the tunnel wall around the intra-articular aperture. As such, embodiments disclosed herein may minimize bungee-cord-like motion of a graft or implant within a bone tunnel.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:

1. A method of preparing a bone block assembly for surgery, the method comprising:
   providing a bone block having a proximal end, a distal end, a central axis defined therethrough, and a hole formed at the distal end along an axis that is divergent from the central axis of the bone block; and
   disposing a threaded screw into the bone block along an axis that is divergent from the central axis of the bone block, the threaded screw having a first eyelet formed on a proximal end of the threaded screw, wherein the first eyelet of the threaded screw is configured to receive a suture.

2. The method of claim 1 wherein the first eyelet of the threaded screw is, at least partially, exposed on a proximal end of the bone block when the threaded screw is fully disposed within the bone block.

3. The method of claim 1 wherein at least one graft is coupled to the bone block.

4. The method of claim 1 further comprising disposing a suture through the first eyelet of the threaded screw.

5. A method of delivering a bone block assembly into a body, the method comprising:
   providing a bone block having a proximal end, a distal end, a central axis defined therethrough, and a hole formed at the distal end along an axis that is divergent from the central axis of the bone block, the bone block having a threaded screw disposed therein, the threaded screw having a first eyelet formed on a proximal end of the threaded screw and a suture disposed through the first eyelet of the threaded screw;
   forming a tunnel through a bone in a body; and
   suspending the bone block within the tunnel formed through the bone with a fixation device.

6. The method of claim 5 wherein at least one graft is coupled to the bone block.

7. The method of claim 5 further comprising:
disposing the suture into the tunnel formed through the bone; and pulling the bone block into the tunnel by the suture.

8. The method of claim 5 wherein suspending the bone block within the tunnel formed through the bone with the fixation device comprises securing the suture on a surface of the bone.

9. The method of claim 1 wherein the threaded screw is cannulated.

10. The method of claim 5 wherein the threaded screw is cannulated.

11. The method of claim 1 further comprising a second eyelet formed on a distal end of the threaded screw.

12. The method of claim 11 wherein the second eyelet is configured to receive a suture.

13. The method of claim 5 further comprising a second eyelet formed on a distal end of the threaded screw.

14. The method of claim 13 wherein the second eyelet is configured to receive a suture.

15. The method of claim 5 wherein the fixation device has at least one hole formed therein.

16. The method of claim 15 wherein the at least one hole of the fixation device is configured to receive the suture.

\* \* \* \* \*